United States Patent
Iding et al.

(10) Patent No.: US 6,518,048 B2
(45) Date of Patent: Feb. 11, 2003

(54) STEREO-SPECIFIC SYNTHESIS OF SHIMIKIC ACID DERIVATIVES WITH IMPROVED EFFICIENCY

(75) Inventors: Hans Iding, Rheinfelden (DE); Beat Wirz, Reinach (CH); Ulrich Zutter, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/811,862

(22) Filed: Mar. 19, 2001

(65) Prior Publication Data

US 2001/0036653 A1 Nov. 1, 2001

(30) Foreign Application Priority Data

Apr. 10, 2000 (EP) .............................. 00107669

(51) Int. Cl.⁷ ..................... C12P 13/00; C12P 13/02
(52) U.S. Cl. ...................... 435/128; 435/129
(58) Field of Search ................... 435/128, 129

(56) References Cited

FOREIGN PATENT DOCUMENTS

EP        98/07685         2/1998

OTHER PUBLICATIONS

John C. Rohloff et al., *Practical Total Synthesis of the Anti–Influenza Drug GS–4104*, J.Org. Chem., vol. 63, pp. 4535–4550 (1998).

*Primary Examiner*—Herbert J. Lilling

(74) *Attorney, Agent, or Firm*—George W. Johnston; Patricia S. Rocha-Tramaloni

(57) ABSTRACT

The invention provides a multistep synthesis for the preparation of 4,5-diamino shikimic acid derivatives of formula

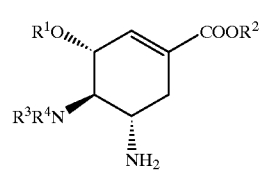

Ia starting from an isophthalic acid derivative of formula

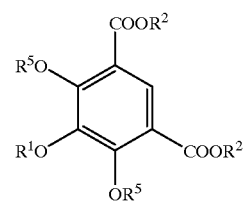

II 4,5-Diamino shikimic acid derivatives are potent inhibitors of viral neuraminidase.

11 Claims, No Drawings

STEREO-SPECIFIC SYNTHESIS OF SHIMIKIC ACID DERIVATIVES WITH IMPROVED EFFICIENCY

FIELD OF INVENTION

The present invention is related to stereo-specific synthesis and more particularly to a method of preselecting S or R stereo-isomerism of shikimic acid derivatives and a process for producing these compounds from readily available low-cost starting materials.

BACKGROUND OF THE INVENTION

The present invention relates to a multi-step process for the preparation of 4,5-diamino shikimic acid derivatives, especially for the preparation of (3R,4R,5S)-4-acetamido-5-amino-3-(1-ethylpropoxy)-1-cyclohexene-1-carboxylic acid ethylester and its pharmaceutically acceptable addition salts starting from isophthalic acid derivatives, individual process steps thereof, as well as new specific intermediates.

4,5-diamino shikimic acid derivatives, especially the (3R,4R,5S)-4-acetamido-5-amino-3-(1-ethylpropoxy)-1-cyclohexene-1-carboxylic acid ethylester and its pharmaceutically acceptable addition salts are potent inhibitors of viral neuraminidase (J. C. Rohloff et al., J. Org. Chem., 1998, 63, 4545–4550; WO 98/07685).

A multi step synthesis of (3R,4R,5S)-4-acetamido-5-amino-3-(1-ethylpropoxy)-1-cyclohexene-1-carboxylic acid ethylester from (–)-quinic acid or (–)-shikimic acid is described in (J. C. Rohloff et al, loc.cit.).

Both (–)-quinic acid and (–)-shikimic acid are starting compounds which are rather expensive and hardly accessible in technical quantities. A multi-step synthesis capable to run on a technical scale should therefore preferably be based on starting compounds which are more attractive in price and available in technical quantities.

SUMMARY OF THE INVENTION

A process of the present invention for preparing a 4,5 di amino shikimic acid derivitive having formula 1a

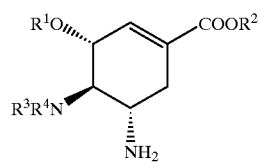

wherein $R^1$ is an optionally substituted alkyl group, $R^2$ is an alkyl group and $R^3$ and $R^4$, independently of each other are H or a substituent of an amino group, with the proviso that both $R^3$ and $R^4$ are not H includes hydrogenating an isophthalic acid derivative of formula II;

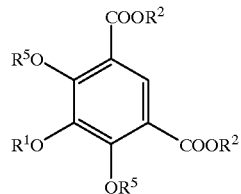

wherein $R^5$ is H or lower alkyl thereby forming an all-cis-cyclohexane dicarboxylate of formula III;

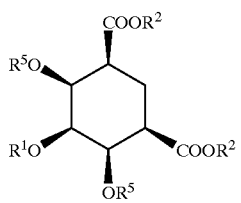

then selecting a stereo-selective hydrolysis and dealkylation sequence from the group consisting of: a) in the case when $R^5$=H, stereo-selectively hydrolyzing the all-cis-cylohexane dicarboxylate of formula (III), thus forming the (S)- or (R)-cyclohexane monoacid of formula IVa or IVb, b) in the case where $R^5$=lower alkyl, stereo-selectively hydrolyzing the alkoxy all-cis-cyclohexane dicarboxylate of formula (III), dealkylating to form the (S)- or (R)-cyclohexane monoacid of formula IVa or IVb and c) in the case where $R^5$=lower alkyl, dealkylating the alkoxy all-cis-cyclohexane dicarboxylate of formula (III) and then stereo-selectively hydrolyzing the all-cis-cyclohexane dicarboxylate of formula (III) to form the (S)- or (R)-cyclohexane mono acid of the formulae IVa or IVb;

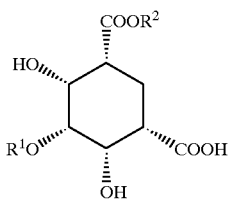

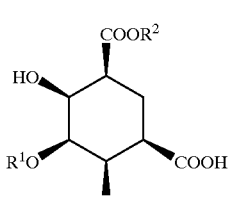

converting the cyclohexane monoacid of formula (IVa) to an oxazolidinone of the formula Va;

Va

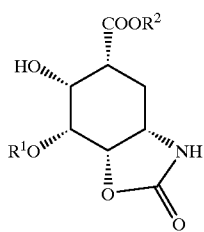

transforming the oxazolidinone (Va) into a cyclohexenol (VIa)

VIa

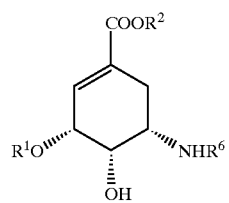

wherein $R^6$ is an amino protecting group; converting cyclohexenol (VIa) to an azide VIIa; and VIIa

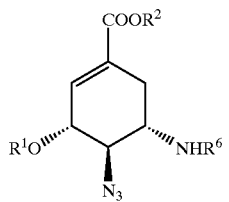

reducing and acylating azide (VIIa); forming the respective acylated amine (VIIIa)

VIIIa

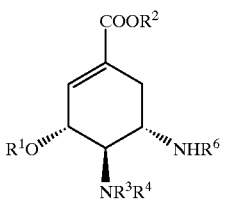

thereby forming the 4,5-diamino shikimic acid derivative (Ia) by removing the amino protecting group $R^6$. In performing the series of steps of the process of the invention, the steps forming compounds from IVa are exemplary of similar steps forming a similar series of compounds from IVb to VIIIb. This alternate series of steps are equally preferred.

The stereo-selective synthethic method of the invention allows the use of lower-cost more accessible starting materials, provides the practitioner the ability to preselect the desired stereochemistry at several chiral centers on the molecule by selecting either an esterase or a lipase, thereby greatly improving the efficiency and accessiblity to shikimic acid derivatives that are known to be potent inhibitors of viral neuraminidase.

DETAILED DESCRIPTION OF THE INVENTION

The preferred embodiments of the invention are described herein in detail and should be considered exemplary, not limitive. The scope of the invention is measured by the appended claims and their equivalents. The present invention relates to a process for the preparation of a 4,5-diamino shikimic acid derivatives of formula Ia Ia

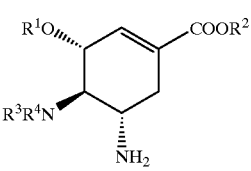

and pharmaceutically acceptable addition salts thereof wherein $R^1$ is an optionally substituted alkyl group, $R^2$ is an alkyl group and $R^3$ and $R^4$, independent of each other are H or a substituent of an amino group, with the proviso that both $R^3$ and $R^4$ are not H and which is characterized in that in step a)

an isophthalic acid derivative of the formula

II

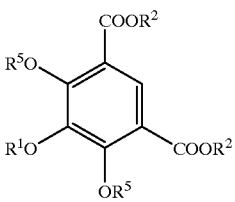

wherein $R^1$ and $R^2$ are as above and $R^5$ is H or lower alkyl is hydrogenated to form an all-cis-cyclohexane dicarboxylate of the formula

III

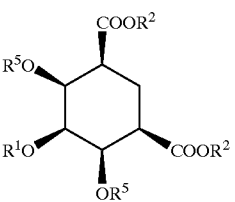

wherein $R^1$, $R^2$ and $R^5$ are as above, in step b)

the cyclohexane dicarboxylate of formula (III) is, if $R^5$=H, stereo-selectively hydrolyzed to form the (S)- or (R)-cyclohexane monoacid of formulas IVa or IVb or, if $R^5$=lower alkyl, either dealkylated first and then stereo-selectively hydrolyzed or stereo-selectively hydrolyzed first and then dealkylated to form the (S)- or (R)-cyclohexane mono acid of the formula IVa

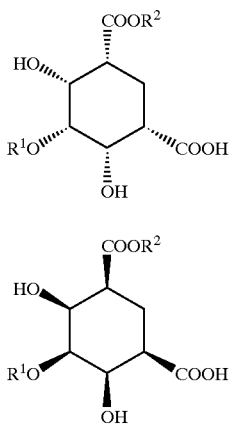

wherein $R^1$ and $R^2$ are as above, in step c)

the cyclohexane monoacid of the formula (IVa) is further converted to an oxazolidinone of the formula Va

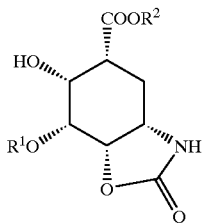

wherein $R^1$ and $R^2$ are as above, in step d)

the oxazolidinone of formula (V) is transformed into a cyclohexenol of the formula VIa

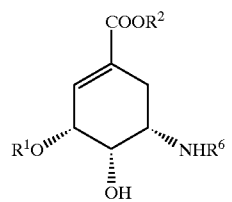

wherein $R^1$ and $R^2$ are as above and $R^6$ is an amino protecting group in step e)

the cyclohexenol of formula (VI) is further converted into an azide of formula

VIIa

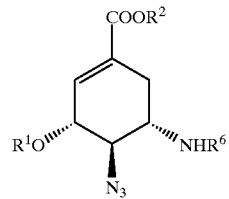

wherein $R^1$, $R^2$ and $R^6$ are as above, in step f)

the azide of formula (VII) is reduced and acylated to form the acylated amine of the formula VIIIa

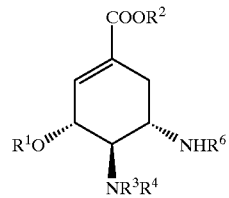

wherein $R^1$, $R^2$, $R^3$, $R^4$ and $R^6$ are as above, and in step g) the acylated amine of the formula (VIII) is finally transferred into the 4,5-diamino shikimic acid derivative of formula (I) by removing the amino protecting group $R^6$ and if necessary by forming the respective pharmaceutically acceptable salt.

The term alkyl in $R^1$ has the meaning of a straight chain or branched alkyl group of 1 to 20 C-atoms, expediently of 1 to 12 C-atoms. Examples of such alkyl groups are methyl, ethyl, n-propyl, i-propyl, n-butyl, i-butyl, tert-butyl, pentyl and its isomers, hexyl and its isomers, heptyl and its isomers, octyl and its isomers, nonyl and its isomers, decyl and its isomers, undecyl and its isomers and dodecyl and its isomers. This alkyl group can be substituted with one or more substituents as defined in e.g. WO 98/07685. Suitable substituents are alkyl of 1 to 6 C-atoms (as defined above), alkenyl of 2 to 6 C-atoms, cycloalkyl with 3 to 6 C-atoms, hydroxy, alkoxy with 1 to 6 C-atoms, alkoxycarbonyl with 1 to 6 C-atoms, F, Cl, Br, and J.

Preferred meaning for $R^1$ is 1-ethylpropyl.

$R^2$ is a straight chain or branched alkyl group of 1 to 12 C-atoms, expediently of 1 to 6 C-atoms as exemplified above.

Preferred meaning for $R^2$ is ethyl.

$R^5$ is a lower n-alkyl group of 1 to 3 C-atoms, preferably methyl.

$R^3$ and $R^4$ are substituents of an amino group used and known in the art and described e.g. in WO 98/07685.

$R^3$ and $R^4$ preferably stand for alkanoyl groups, more preferably lower alkanoyl with 1 to 6 C-atoms such as hexanoyl, pentanoyl, butanoyl (butyryl), propanoyl (propionyl), ethanoyl (acetyl) and methanoyl (formyl). Preferred alkanoyl group and therefore preferred meaning for $R^3$ is acetyl and for $R^4$ is H.

$R^6$ is a common amino protecting group used and known in the art and described e.g. in "Protective Groups in Organic Chemistry", Theodora W. Greene et al., John Wiley & Sons Inc., New York, 1991, 315–385.

$R^6$ suitably is benzyloxycarbonyl (Z), tert-butyloxycarbonyl (BOC), allyloxycarbonyl (AllOC) or 9-fluorenylmethoxycarbonyl (FMOC), preferably tert-butoxycarbonyl (BOC).

Preferred 4,5-diamino shikimic acid derivative of formula (I) is the (3R,4R,5S)-4-acetamido-5-amino-3-(1-ethylpropoxy)-1-cyclohexene-1-carboxylic acid ethylester and the (3R,4R,5S)-4-acetamido-5-amino-3-(1-ethylpropoxy)-1-cyclohexene-1-carboxylic acid ethyl ester phosphate (1:1).

The process of the present invention from step c) onwards run with the cyclohexane monoacid of the formula (IVb) retains the stereo-specificity introduced in the stereo-selective hydrolysis of the cyclohexane dicarboxylate and produces the (+)-enantiomer of the 4,5-diamino shikimic acid derivative having the formula

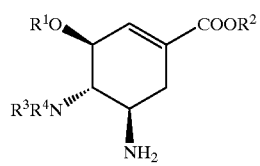
Ib wherein $R^1$, $R^2$, $R^3$ and $R^4$ are as above and all the (+)-enantiomers of the corresponding intermediates.

Step a)

Step a) comprises the hydrogenation of an isophthalic acid derivative of the formula (II) to an all-cis-cyclohexane dicarboxylate of the formula (III).

Hydrogenation takes place with hydrogen in the presence of a common hydrogenation catalyst which may be applied on an inert support. Suitable hydrogenation catalysts are rhodium or ruthenium applied in an amount of 1 to 10% on an inert support, such as on aluminum oxide or charcoal. The hydrogenation can be effected in an inert solvent like ethylacetate, ethanol, tetrahydrofuran or tert-butyl methyl ether at temperatures between 20° C. and 150° C. and at hydrogen pressures between 1 bar and 200 bar.

The resulting cyclohexane dicarboxylate of the formula (III) shows an all-cis meso form and therefore is optically inactive.

Step b)

Step b) comprises a stereo-selective enzymatic hydrolysis and, if necessary, a dealkylation of the cyclohexane dicarboxylate of the formula (III) to either the (S)- or (R)-cyclohexane mono acid of the formulas (IVa) or (IVb).

Starting from the cyclohexane dicarboxylate of formula (III) with $R^5$=H stereo-selective enzymatic hydrolysis can directly take place, however, starting from the cyclohexane dicarboxylate of formula (III) with $R^5$=lower alkyl dealkylation can either take place before or after the stereo-selective hydrolysis.

The dealkylation, can take place with an alkali iodide in the presence of a trialkylhalogen silane. Dealkylation preferably is a demethylation and preferably sodium iodide together with trimethylchlorosilane is used. This dealkylation as a rule is performed in an inert solvent, such as in acetonitrile at temperatures between 20° C. and 80° C.

Stereo-selective hydrolysis comprises an enzymatic hydrolysis of the cyclohexane dicarboxylate of the formula (III), whereby the choice of the enzyme determines whether the (S)-monoacid of the formula

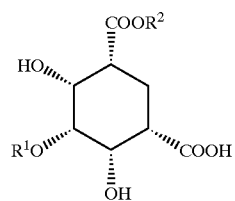
IVa or the (R)-monoacid isomer of the formula

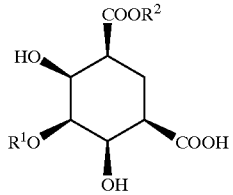
IVb can be obtained.

In order to achieve the 4,5-diamino shikimic acid of formula (Ia) with the desired stereo configuration the subsequent reaction steps are performed with the (S)-monoacid of formula (IVa).

Starting with the all-cis-cyclohexane dicarboxylate of formula III with $R^5$=H suitable enzymes to gain the (S)-isomer of formula (IVa) are esterases of the EC class 3.1.1.1, preferably mammalian esterases (e.g. from pig, bovine or horse). The most preferred enzyme is pig liver esterase (which is subsequently termed PLE). Commercial preparations of PLE can be purchased e.g. from Roche Diagnostics, Fluka, Sigma, Amano or Altus. Also less purified PLE preparations (e.g. 'PLE technical grade' from Roche Diagnostics) or only poorly purified preparations (e.g. such as 'pig liver acetone powder' from Fluka) can be used as well as PLE preparations with enriched or separated isozyme fractions (like e.g. Chirazyme E-1 or Chirazyme E-2 from Roche Diagnostics). As an alternative the enzymes may be used in immobilized form.

The substrate is applied as a suspension in an aqueous solution in a 5–15% concentration (w/w), preferably around 10%. A suitable reaction temperature is room temperature to 35° C., a suitable reaction pH between 6.5 and 8.5.

As to the aqueous phase, common buffer solutions known to be used for biochemical conversions are used like e.g. phosphate or Tris-buffer in a concentration of 5–50 mM. Such a buffer solution can additionally contain a salt like e.g. NaCl or KCl in a concentration of 50 to 300 mM. A preferred buffering system contains 0.1 M KCl and 10 mM Tris-hydrochloride pH 8.0.

After addition of the enzyme the pH of the reaction mixture at the selected value is maintained under stirring by the controlled addition of a base such as NaOH or KOH, whereby the formed monoacid goes into solution and the reaction mixture becomes rather clear.

After termination of the reaction, the product is worked up by acidification of the reaction mixture and extraction with a common organic solvent.

Starting with the all-cis cyclohexane dicarboxylate of formula III with $R^5$=H or lower alkyl, preferably methyl, suitable enzymes to gain the (R)-isomer of formula (IVb) are lipases of the EC class 3.1.1.3. Suitable representatives of this class are the lipases from *Aspergillus oryzae*

(commercially available at Fluka), *Thermomyces lanuginosa* (formerly termed *Humicola lanuginosa*; e.g. from Novo Nordisk) and from *Mucor miehei* (e.g. from Novo Nordisk). Again, also less purified crude enzyme preparations may be used.

Again, as an alternative, the preselected enzymes may be used in immobilized form. The reaction is carried out in an aqueous or an aqueous-organic biphasic system. Preferred is a biphasic system with a water-immiscible apolar solvent as co-solvent. Suitable co-solvents are alkanes or cycloalkanes, preferred is cyclohexane.

The substrate is applied (as a suspension) in the mono- or biphasic system in 5–10% overall concentration (w/w). A suitable reaction temperature is room temperature to 35° C., a suitable reaction pH between 6.5 and 8.5.

As to the aqueous phase, common buffer solutions known to be used for biochemical conversions are used like e.g. phosphate, borate or Tris-buffer in a concentration of 5–50 mM. Such a buffer solution can additionally contain a salt like e.g. NaCl, KCl or a polyhydric alcohol such as a sugar (e.g. glucose) in a concentration of 50 to 300 mM. A preferred buffering system could e.g. contain 0.1 M glucose and 5 mM sodium phosphate pH 7.0. The ratio organic solvent/aqueous phase is in the range of 1:10 to 1:1.

After addition of the enzyme the pH of the reaction mixture is maintained under stirring at the selected value by the controlled addition of a base such as NaOH or KOH.

After termination of the reaction, the product is worked up by acidification of the reaction mixture and extraction with a common organic solvent.

Step c)

Step c) comprises the conversion of the cyclohexane mono acid of the formula (IVa) into the oxazolidinone of formula (V).

This conversion can take place applying the principles of a Curtius or of a Hoffmann degradation. Where in the Hoffmann degradation the oxazolidinone is formed by transformation of the cyclohexane monoacid into the respective cyclohexane monoamide and by subsequent ring formation e.g. with a hypochlorite, the Curtius degradation involves the formation of the cyclohexane azide intermediate.

As a suitable variation of the Curtius degradation a Yamada-Curtius degradation using dialkylphosphorylazides or diarylphosphoryl azides, preferably diarylphosphoryl azides, most preferably diphenyl phosphoryl azide (DPPA) can be applied.

The Yamada-Curtius degradation takes place in the presence of a tertiary amine, preferably triethylamine and in an inert solvent such as e.g. methylene chloride or ethylacetate.

Step d)

Step d) covers the transformation of the oxazolidinone of formula (V) into a cyclohexenol of formula (VI).

This transformation comprises the introduction of an amino protecting group $R^6$ and a subsequent base induced transformation to the cyclohexenol of formula (VI).

Suitable substituents of the amino group $R^6$ are as stated above, however, the BOC group is the preferred group. Introduction of the amino protecting group is known to the skilled in the art.

Suitable base for the subsequent base induced transformation is an alkali-hydride, an alkali-alcoholate, diazabicyclo undecen (DBU) or a tetraalkyl guanidine. Preferred base is sodium hydride applied in amounts of 0.5 to 25 mol %.

Usually the reaction takes place in an inert solvent such as methylene chloride, toluene, tetrahydrofuran, ethyl acetate at reflux temperature of the respective solvent.

The cyclohexenol of formula (VI) can be isolated from the reaction mixture by methods known to the skilled in the art.

Step e)

Step e) comprises the formation of an azide of formula (VII).

This step involves in a first sequence, the transformation of the hydroxy group into a suitable leaving group and in a second sequence, the azide formation, thereby leading to an inversion of configuration at the reaction center.

The transformation of the OH group into a leaving group can be performed by sulfonylation, i.e., converting the OH group into a sulfonic acid ester.

Agents commonly used for producing such sulfonic esters are e.g. the halogenides or the anhydrides of the following sulfonic acids: methane sulfonic acid, p-toluenesulfonic acid a p-nitrobenzenesulfonic acid, p-bromobenzenesulfonic acid or trifluoromethanesulfonic acid.

Preferred agent is a halogenide or anhydride of trifluoro methane sulfonic acid such as trifluoro methane sulfonic anhydride.

The sulfonylating agent is expediently added in an amount of 1.0 to 1.5 equivalents relating to one equivalent of the cyclohexenol of formula VI in presence of about two equivalents of a suitable base.

The reaction usually takes place in an inert solvent such as in methylene chloride and at reaction temperatures between −20° C. and room temperature.

The sulfonic acid ester formed can be isolated and purified, e.g. by crystallization or directly be introduced into the following reaction sequence.

Azide formation is effected by treating the sulfonic acid ester intermediate previously obtained with a suitable azide whereby inversion of the configuration takes place. Azides commonly used are alkaliazides like sodium azide in amounts of 1 to 2 equivalents.

The reaction takes place in a solvent such as in dimethyl sulfoxide, N,N-dimethylformamide, ethanol or acetone at temperatures between −10° C. and 50° C.

Step f)

Step f) covers the reduction of the azide and the subsequent acylation of the resulting amine to form the respective acylated amine of the formula (VIII).

Reduction takes place either by a) a classical metal catalysed hydrogenation with hydrogen or b) by reduction of the azide with a phosphine.

According to method a) common hydrogenation catalysts such as e.g. Pd, Pt, Raney-Ni or Raney-Co catalysts which may be applied on an inert support can be used.

The hydrogenation can take place in a suitable organic solvent e.g. in ethylacetate at temperatures between 20° C. and 60° C. at at hydrogen pressures between 1 and 50 bar.

Phosphines which according to method b) can suitably be used are trioctyl phosphine, triisobutyl phosphine and tri-n-butyl phosphine. Most preferred phosphine is the tri-n-butyl phosphine.

Typically the reduction is performed in a polar solvent such as in ethylacetate or in tetrahydrofuran in presence of 1 to 20 equivalents of water. The reaction temperature, depending on the phosphine used, as a rule is chosen in the range of −20° C. and 50° C. The amine formed can be isolated but is preferably directly acylated in the following reaction sequence.

Acylation can be effected using acylating agents in the presence of a base and at conditions known to the skilled in the art. Suitable acylating agents as a rule are aliphatic or aromatic carboxylic acid halides or anhydrides. Preferred acylating agents are the acetylating agents such as acetyl chloride or acetanhydride.

Step g)

Step g) comprises the removal of the amino protecting group $R^6$ and, if necessary, the formation of the respective pharmaceutically acceptable salt of the 4,5-diamino shikimic acid derivative of formula (I).

The amino protecting group $R^6$ can be removed following methods well known to the skilled in the art. The preferred BOC group can e.g. easily be split off with HBr in acetic acid at room temperature or with HCl in ethylacetate. The free amine can then be liberated with e.g. an aqueous base and then further be transformed into the pharmaceutically acceptable addition salt following the methods described in J. C. Rohloff et al., J. Org. Chem. 63, 1998, 4545–4550; WO 98/07685).

The term "pharmaceutically acceptable acid addition salts" embraces salts with inorganic and organic acids, such as hydrochloric acid, hydrobromic acid, nitric acid, sulfuric acid, phosphoric acid, citric acid, formic acid, fumaric acid, maleic acid, acetic acid, succinic acid, tartaric acid, methane sulfonic acid, p-toluenesulfonic acid and the like.

The salt formation is effected at room temperature in accordance with methods which are known per se and which are familiar to any person skilled in the art.

The preferred pharmaceutically acceptable acid addition salt is the 1:1 salt with phosphoric acid which can be formed preferably in ethanolic solution at a temperature of −20° C. to 50° C.

The invention further comprises a process for the preparation of an isophthalic acid derivative of the formula

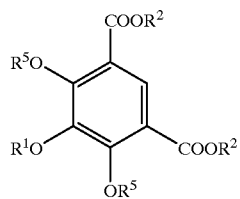

II wherein $R^1$, $R^2$ and $R^5$ are as above
which is characterized in that a dialkoxyphenol of the formula

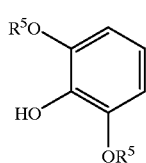

X wherein $R^5$ is as above
is
in step aa)
converted into a trialkoxybenzene of the formula

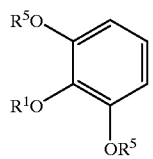

XI wherein $R^1$ and $R^5$ are as above,
and in step ab) further halogenated to a dihalotrialkoxy benzene of the formula

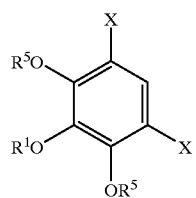

XII wherein $R^1$ and $R^5$ are as above and X stands for a halogen atom and finally in step ac)

carbonylated to form the product of the formula II.

Step aa)

Etherification of the dialkyloxyphenol of formula X can be performed with the methane sulfonic acid ester of the respective alcohol $R^1OH$. Reaction as a rule takes place in the presence of a strong base such as an alkali alcoholate in an inert solvent.

Alternatively etherification can happen under Mitsunobu conditions (O. Mitsunobu, Synthesis, 1981, 1) i.e. by treatment of the dialkoxyphenol of formula X with the respective alcohol $R^1OH$ in the presence of diisopropyl azodicarboxylate (DIAD) and triphenyl phosphine in a suitable inert solvent like tetrahydrofuran.

Step ab)

The halogenation in this step preferably is a dibromination.

A suitable bromination agent for the trialkoxybenzene of formula XI is e.g. N-bromo succinimide (NBS).

Dibromination usually takes place with 2 equivalents NBS in a polar solvent such as in N,N-dimethylformamide at temperatures between −10° C. and 50° C.

Step ac)

Carbonylation of the dihalotrialkoxybenzene of formula XII can be performed with carbon monoxide in the presence of suitable catalyst in an alcoholic solvent like ethanol.

Suitable catalysts are metal complexes formed by a metal compound of the group VIII element of the periodic table and a phosphine compound e.g. of palladium acetate and 1,3-bis (diphenyl phosphino) propane (dppp) or triphenylphosphine.

Usually the reaction is performed at temperatures of 80° C. to 150° C. and at CO-pressures up to 20 bar.

The invention further comprises a process for the preparation of an all-cis-cyclohexane dicarboxylate derivative of the formula

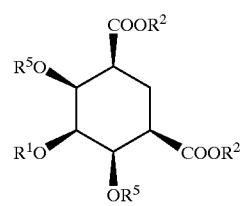

III wherein $R^1$, $R^2$ and $R^5$ are as above
which is characterized in that an isophthalic acid derivative of the formula

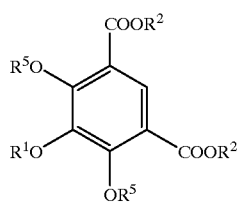

II wherein $R^1$, $R^2$ and $R^5$ are as above is hydrogenated.

This step is identical to step a) of the multi-step synthesis described herein above. The respective description of step a) is incorporated herein by reference.

The invention further comprises a stereo-selective hydrolysis and, if necessary, a dealkylation of an all-cis-cyclohexane dicarboxylate of the formula

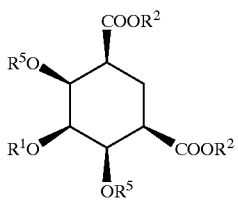

III wherein $R^1$, $R^2$ and $R^5$ are as above, to form the (S)- or (R)-cyclohexane monoacid of the formulas.

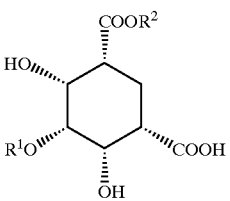

IVa

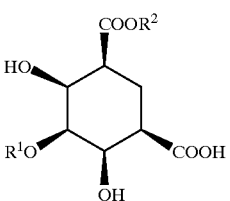

IVb wherein $R^1$ and $R^2$ are as above.

This step is equivalent to step b) of the multi-step synthesis described herein above. The respective description of step b) is incorporated herein by reference.

The following key intermediates are new and not known to the state of the art, they accordingly are an essential element of the present invention.

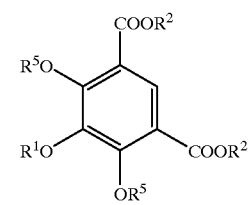

II wherein $R^1$, $R^2$ and $R^5$ are as above, preferably 5-(1-ethyl-propoxy)-4,6-dimethoxy isophthalic acid ethyl ester with $R^1$=1-ethyl-propyl, $R^2$=ethyl and $R^5$=methyl.

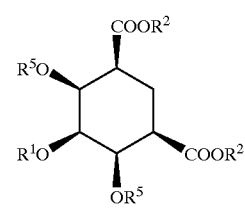

III wherein $R^1$, $R^2$ and $R^5$ are as above, preferably all-cis-5-(1-ethyl-propoxy)-4,6-dimethoxy-cyclohexane-1,3-dicarboxylic acid diethylester with $R^1$=1-ethyl propyl, $R^2$=ethyl and $R^5$=methyl and all-cis-5-(1-ethyl-propoxy)-4,6-dihydroxy-cyclohexane-1,3-dicarboxylic acid diethylester with $R^1$=1-ethyl propyl, $R^2$=ethyl and $R^5$=H.

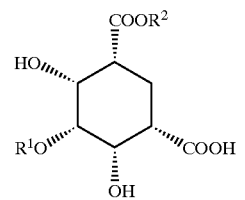

IVa wherein $R^1$ and $R^2$ are as above, preferably all-cis-(1R, 3S,4S,5S,6R)-5-(1-ethyl propoxy)-4,6-dihydroxy cyclohexane-1,3-dicarboxylic acid 1-ethyl ester with $R^1$=1-ethyl propyl, $R^2$=ethyl

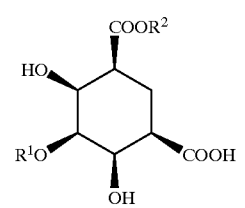

IVb wherein $R^1$ and $R^2$ are as above, preferably all-cis-(1S,3R, 4R,5R,6S)-5-(1-ethyl propxy)-4,6-dihydroxy cyclohexane-1,3-dicarboxylic acid 1-ethyl ester with $R^1$=1-ethyl propyl, $R^2$=ethyl.

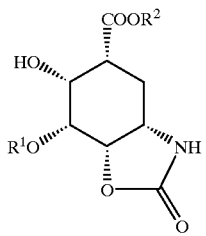

Va

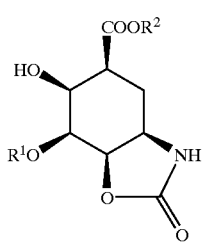

Vb wherein R¹ and R² are as above, preferably (3aS,5R,6R,7R,7aS)-7-(1-ethyl propoxy)-6-hydroxy-2-oxo-octahydrobenzooxazole-5-carboxylic acid ethyl ester with R¹=1-ethyl propyl and R²=ethyl and (3aR,5S,6S,7S,7aR)-7-(1-ethyl propoxy)-6-hydroxy-2-oxo-octahydrobenzooxazole-5-carboxylic acid ethyl ester with R¹=1-ethyl propyl and R²=ethyl.

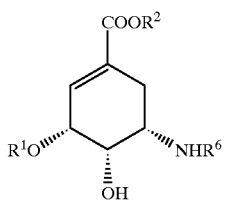

VIa

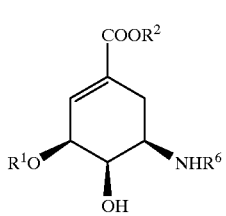

VIb wherein R¹, R² and R⁶ are as above, preferably (3R,4S,5S)-5-tert.-butoxy carbonyl-amino-3-(1-ethyl-propoxy)-4-hydroxy cyclohex-1-ene carboxylic acid ethyl ester (VIa) with R¹=1-ethyl propyl, R¹=ethyl and R⁶=tert-butoxy carbonyl and (3S,4R,5R)-5-tert-butoxy carbonyl-amino-3-(1-ethyl-propoxy)-4-hydroxy cyclohex-1-ene carboxylic acid ethyl ester (VIb) with R¹=1-ethyl propyl, R²=ethyl and R⁶=tert-butoxy carbonyl.

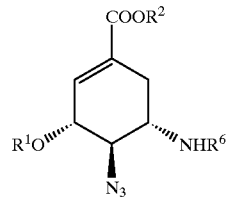

VIIa

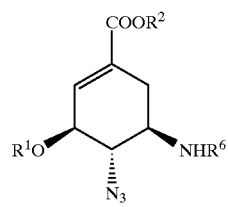

VIIb wherein R¹, R² and R⁶ are as above, preferably (3R,4R,5S)-4-azido-5-tert.-butoxy carbonylamino-3-(1-ethyl propoxy) cyclohex-1-ene carboxylic acid ethyl ester (VIIa) with R¹=1-ethyl propyl, R²=ethyl and R⁶=tert-butoxy carbonyl and (3S,4S,5R)-4-azido-5-tert.-butoxy carbonylamino-3-(1-ethyl propoxy) cyclohex-1-ene carboxylic acid ethyl ester (VIIb) with R¹=1-ethyl propyl, R²=ethyl and R⁶=tert-butoxy carbonyl The following examples shall illustrate the invention in more detail without limiting it.

EXAMPLE 1

Preparation of Methanesulfonic Acid 1-ethyl-propyl ester

To a colorless solution of 88.15 g 3-pentanol (1.0 mol) in 150 ml pyridine were added under stirring at 0° C. 126.0 g methanesulfonyl chloride (1.1 mol) over 1 h. After warming up (15 min.) and stirring at room temperature for 1 h, 50 ml deionized water were added all at once and stirring at room temperature was continued for 1 h. The reaction mixture was diluted with 500 ml ethyl acetate and washed with 800 ml 1N HCl and 250 ml 10% brine. Both aqueous layers were extracted sequentially with 250 ml ethyl acetate. After drying the combined organic layers over ca. 20 g $Na_2SO_4$, the solvent was removed on the rotary evaporator (50° C./≧1 mbar) affording 154.4 g (92.9%) yellow, oily title product, which could be used in the next step without purification.

EXAMPLE 2

Preparation of (1-ethyl-propoxy)-1,3-dimethoxy-benzene

To a yellow solution of 38.5 g 2,6-dimethoxy phenol (0.25 mol) and 83.1 g methanesulfonic acid 1-ethyl-propyl ester (0.50 mol) in 500 ml dimethylsulfoxide was added under stirring at 50° C. a solution of 56,1 g potassium tert-butylate (0.50 mol) in 500 ml dimethylsulfoxide over 4 h. After additional 2.8 g potassium tert-butylate (0.025 mol) were added, stirring at 50° C. was continued for 1h. The reaction mixture was distributed between 500 ml ethyl acetate and 600 ml 1N HCl. The organic layer was washed twice with 250 ml, a total of 500 ml deionized water and the aqueous layers were extracted sequentially with 250 ml ethyl acetate.

The combined organic layers were dried over ca. 25 g $Na_2SO_4$, filtered and the solvent was evaporated by rotary evaporation (50° C./≧1 mbar) affording 56.2 g (100.2%) of the title product as an orange oil, which was used without purification in the next step (bp. 90° C./0.03 mbar).

EXAMPLE 3
Preparation of 1,5-dibromo-3-(1-ethyl-propoxy)-2,4-dimethoxy-benzene)

To a solution of 44.9 g crude (1-ethyl-propoxy)-1,3-dimethoxy-benzene (0.20 mol) in 60 ml N,N-dimethylformamide was added at 0° C. a solution of 73.4 g N-bromosuccinimide (0.4 mol) in 160 ml N,N-dimethylformamide over 1 h. After warming to room temperature (0.5 h) and stirring at ambient temperature for 18 h, the red-brown reaction mixture was distributed between 400 ml ethyl acetate and 400 ml 5% brine. The organic layer was washed twice with 200 ml, a total of 400 ml 5% brine and all aqueous layers were extracted sequentially with 200 ml ethyl acetate. The combined organic layers were stirred with ca. 4 g charcoal for 1 h, filtered over ca. 20 g filter aid (Hyflo). Removal of the solvent by rotary evaporation (50° C./≧1 mbar) afforded 78.7 g (103%) crude title product which was dissolved in 400 ml 80% (v/v) ethanol-$H_2O$ at 50° C. Crystallization by cooling down and stirring at 20° C. for 18 h afforded after filtration and washing with ca. 40 ml –20° cold 80% (v/v) ethanol-$H_2O$ and drying (35° C./1 mbar/18 h) 69.0 g (90.3%) light yellow title product, m.p. 47–48° C.

EXAMPLE 4
Preparation of 5-(1-ethyl-propoxy)-4,6-dimethoxy-isophthalic acid diethyl ester The autoclave was charged with 38.21 g 1,5-dibromo-3-(1-ethyl-propoxy)-2,4-dimethoxy-benzene (0.10 mol), 39.26 g potassium acetate (0.40 mol), 200 ml ethanol, 0.11 g palladium(II)acetate (0.5 mmol) and 0.25 g 1,3-bis(diphenyl-phosphino)propane (0.6 mmol). The autoclave was sealed, pressurized and vented four times with 10 bar of carbon monoxide with stirring (200 rpm) and finally the reaction mixture was heated to 110° C. with stirring (600 rpm). The CO pressure was adjusted to 10 bar and the reaction was continued at constant pressure (10 bar at 110° C.) for 15 h. After cooling down, the autoclave was vented and the reaction mixture poured to a stirred mixture of 100 ml hexane and 200 ml 5% aqueous $Na_2CO_3$. The aqueous layer was separated and extracted with 100 ml hexane. Both organic layers were washed sequentially with 100 ml 1N HCl, combined and dried over ca. 10 g $Na_2SO_4$. After filtration and removal of the solvent by rotary evaporation (50° C./≧1 mbar) the resulting 35.7 g yellow, oily residue were distilled on the high vacuum, affording 34.9 g (94.6%) of the title product as a light yellow oil, b.p. 140° C./0.02 mbar.

EXAMPLE 5
Preparation of all-cis-5-(1-ethyl-propoxy)-4,6-dimethoxy-cyclohexane-1,3-dicarboxylic acid diethyl ester The autoclave was charged with 36.84 g 5-(1-ethyl-propoxy)-4,6-dimethoxy-isophthalic acid diethyl ester (0.10 mol), 36.84 g 5% Ru/$Al_2O_3$ catalyst and 250 ml ethyl acetate. The autoclave was sealed and pressurized three times under stirring with 5 bar of $H_2$. The reaction mixture was then stirred under a pressure of 100 bar $H_2$ at 60° C. for 24 h. After cooling to room temperature, the autoclave was vented and flushed with argon. The black suspension was filtered over ca. 50 g filter aid (Hyflo) and the autoclave as well as the filtercake were washed with ca. 200 ml ethyl acetate. The combined, colorless filtrate was evaporated by rotary evaporation (50° C./≧1 mbar) affording 35.1 g (93.7%) solid, which was dissolved in 530 ml hexane at 50° C. Crystallization by cooling down and stirring at –20° C. for 6 h afforded, after filtration, washing with ca. 50 ml –20° C. cold hexane and drying (50° C./1 mbar/16h) 30.8 g (82.2%) white crystalline title product, m.p. 108–109° C.

EXAMPLE 6
Preparation of all-cis-5-(1-ethyl-propoxy)-4,6-dihydroxy-cyclohexane-1,3-dicarboxylic acid diethyl ester To a suspension of 60.0 g sodium iodide (0.40 mol) in 200 ml acetonitrile were added 0.360 g deionised water (0.02 mol). After stirring at 40° C. for 30 min. 50.6 ml trimethylchlorosilane (0.40 Mol=43.5 g) were added all at once and stirring at 40° C. was continued for 1 h. 37.4 g all-cis-5-(1-ethyl-propoxy)-4,6-dimethoxy-cyclohexane-1,3-dicarboxylic acid diethyl ester (0.10 mol) were added to the white suspension all at once and stirring at 40° C. was continued for 14 h. After cooling to room temperature, the orange suspension was distributed between 500 ml ethyl acetate and 250 ml deionised water while the two layers were decolorized by the addition of ca. 2.5 g sodium thiosulfate. The organic layer was washed twice with 100 ml, a total of 200 ml 10% brine and all three aqueous layers were extracted sequentially with 100 ml ethyl acetate. The combined organic layers were dried over ca. 25 g $Na_2SO_4$, filtered and the solvent was evaporated by rotary evaporation (50° C./≧10 mbar). The white, crystalline residue (34.9 g) was dissolved in 200 ml refluxing methylcyclohexane and crystallized by cooling down and stirring at –20° C. for 16 h. Filtration and washing with ca. 20 ml –20° C. cold methylcyclohexane afforded after drying (50° C./10 mbar/16 h) 33.6 g (97.0%) white title product, m.p. 115–116.5° C.

EXAMPLE 7
Preparation of all-cis-(1R,3S,4S,5S,6R)-5-(1-ethyl-propoxy)-4,6-dihydroxy-cyclohexane-1,3-dicarboxylic acid 1-ethyl ester A suspension of 34.40 g all-cis-5-(1-ethyl-propoxy)-4,6-dihydroxy-cyclohexane-1,3-dicarboxylic acid diethyl ester (0.10 mol) in 390 ml 10 mM Tris-buffer pH 8.0 was heated to 35° C. under vigorous stirring. 3.44 ml pig liver esterase ("technical grade" Roche Diagnostics) were added and the suspension kept at pH 8.0 and 35° C. by the controlled addition (pH-stat) of 1.0 N sodium hydroxide solution under vigorous stirring. After a total consumption over 46 h of 103.3 ml 1.0 N NaOH (1.04 equivalents), the pH of the solution was adjusted to 2.0 with ca. 13 ml 25% HCl. The reaction mixture was extracted three times with 330 ml dichloromethane and the combined organic layers were dried over ca. 100 g $Na_2SO_4$. After filtration and removal of the solvent by rotary evaporation (40° C./≧5 mbar) the residue was dried on the vacuum over night (0.03 mbar) affording 29.52 g (93.4%) of the title product as a colorless gum, which was used without purification in the next step.
$[\alpha]_D$=+7.2° ($CHCl_3$; c=1)

EXAMPLE 8
Preparation of (3aS,5R,6R,7R,7aS)-7-(1-ethyl-propoxy)-6-hydroxy-2-oxo-octahydro-benzooxazole-5-carboxylic acid ethyl ester To a solution of 31.2 g all-cis-(1R,3S,4S,5S,6R)-5-(1-ethyl-propoxy)-4,6-dihydroxy-cyclohexane-1,3-dicarboxylic acid 1-ethyl ester (0.10 mol) in 200 ml dichloromethane were added 10.1 g triethylamine (0.10 mol) and 29.0 g diphenyl phosphoryl azide (0.10 mol). The clear reaction mixture was then stirred under reflux for 16 h. After cooling down it was distributed between 200 ml dichloromethane and 300 ml 1M HCl. The organic layer was washed with 300 ml 5% NaHCO$_3$ and three times with 300 ml, 5% brine. The aqueous layers were extracted sequentially twice with 200 ml, dichloromethane. The combined organic layers were dried with ca. 50 g Na$_2$SO$_4$, filtered and the solvent was evaporated by rotary evaporation (35° C./≧10 mbar). The white, crystalline residue (34.6 g) was dissolved in 300 ml refluxing butyl acetate and crystallized by cooling down an stirring at –20° C. for 16 h. Filtration and washing with ca. 40 ml –20° C. cold butyl acetate afforded after drying (50° C./10 mbar/16 h) 25.4 g (80.5% over two steps) white, crystalline title product, m.p. 180–181° C.

[α]$_D$=+31.2° (CHCl$_3$; c=1)

EXAMPLE 9

Preparation of (3R,4S,5S)-5-tert.-butoxycarbonylamino-3-(1-ethyl-propoxy)-4-hydroxy-cyclohex-1-ene carboxylic acid ethyl ester To 2.40 g di-tert-butyl dicarbonate (11 mmol), 25 mg 4-dimethyl-aminopyridine (0.2 mmol) and 3.15 g (3aS,5R,6R,7R,7aS)-7-(1-ethyl-propoxy)-6-hydroxy-2-oxo-octahydro-benzooxazole-5-carboxylic acid ethyl ester (10 mmol) were added 50 ml toluene and the suspension was stirred at room temperature for 4 h. The solvent was removed by rotary evaporation (50° C./10 mbar) and the gummy residue was redissolved in 50 ml toluene. After the addition of 1.15 g tetramethylguanidine (10 mmol) the reaction mixture was refluxed for 20 h, cooled to room temperature and washed with 20 ml 2N HCl and twice with 20 ml, a total of 40 ml 10% brine.

The aqueous layers were extracted sequentially with 25 ml toluene, the organic layers were combined and dried over Na$_2$SO$_4$. Filtration and rotary evaporation (50° C./10 mbar) gave 3.80 g crystalline residue, which was dissolved in 70 ml hot hexane (60° C.) and crystallized by cooling down and stirring over night at –20° C. Filtration and washing with ca. 10 ml –20° C. cold hexane afforded after drying (50° C./10 mbar/16 h) 2.88 g (77.6%) white, crystalline title product, m.p. 102–102.5° C.

[α]$_D$=–52.50° (CHCl$_3$; c=1)

EXAMPLE 10a

Preparation of (3R,4S,5S)-5-tert.-butoxycarbonylamino-3-(1-ethyl-propoxy)-4-trifluoromethanesulfonyloxy-cyclohex-1-enecarboxylic acid ethyl ester A solution of 3.71 g (3R,4S,5S)-5-tert.-butoxycarbonylamino-3-(1-ethyl-propoxy)-4-hydroxy-cyclohex-1-ene carboxylic acid ethyl ester) (10 mmol) and 1.61 ml pyridine (20 mmol) in 20 ml CH$_2$Cl$_2$ was cooled to 0° C. 1.73 ml trifluoro-methanesulfonic anhydride (10.5 mmol) were added over 10 min. and stirring at 0° C. was continued for 1 h. The reaction mixture was washed with 10 ml 1N HCl and twice with 10 ml, a total of 20 ml 10% brine. The aqueous layers were extracted sequentially with 10 ml methylene chloride and the combined organic layers were dried over Na$_2$SO$_4$. Filtration and rotary evaporation (30° C./10 mbar) gave 4.96 g (98.4%) beige, crystalline title product, which was used without further purification in the next step.

EXAMPLE 10b

Preparation of (3R,4S,5S)-5-tert.-butoxycarbonylamino-3-(1-ethyl-propoxy)-4-trifluoromethanesulfonyloxy-cyclohex-1-enecarboxylic acid ethyl ester To 4.80 g di-tert-butyl dicarbonate (22 mmol), 49 mg 4-dimethyl- aminopyridine (0.4 mmol) and 6.31 g (3aS,5R,6R,7R,7aS)-7-(1-ethyl-propoxy)-6-hydroxy-2-oxo-octahydro-benzooxazole-5-carboxylic acid ethyl ester (20 mmol) were added 100 ml toluene and the suspension was stirred at room temperature for 4 h. After the addition of 20 mg 60% sodium hydride dispersion in oil (ca. 0.5 mmol), the reaction mixture was refluxed for 1 h, cooled to room temperature and the solvent was removed by rotary evaporation. The yellowish, semi-crystalline crude (3R,4S,5S)-5-tert.-butoxycarbonylamino-3-(1-ethyl-propoxy)4-hydroxy-cyclohex-1-ene carboxylic acid ethyl ester (7.83 g) was redissolved in 100 ml CH$_2$Cl$_2$ and 3.22 ml pyridine (40 mmol) were added under stirring. After cooling to –10° C., 3.47 ml trifluoromethanesulfonic anhydride (21 mmol) were added by a syringe over 10 min and stirring at –10° C. was continued for 1 h. 20 ml 1N HCl were added to the –10° C. cold reaction mixture under stirring and the organic layer was washed twice with 20 ml, a total of 40 ml 10% brine. All aqueous layers were extracted sequentially with 20 ml CH$_2$Cl$_2$ and the combined organic layers were dried over Na$_2$SO$_4$, filtered and the solvent was removed by rotary evaporation (30°/≧10 mbar). The yellow, crystalline residue (10.0 g) was dissolved in 150 ml hot diisopropyl ether (68° C.) and transferred into a new flask. After cooling to room temperature the suspension was stirred over night at –20° C. Filtration and washing with ca. 40 ml –20° C. cold diisopropyl ether afforded after drying (50° C./10 mbar/16 h) 8,35 g (82.9%) white, crystalline title product, m.p. 122–123° C.

[α]$_D$=–79.1° (CHCl$_3$; c=1)

EXAMPLE 11

Preparation of (3R,4R,5S)-4-azido-5-tert.-butoxycarbonylamino-3-(1-ethyl-propoxy)-cyclohex-1-enecarboxylic acid ethyl ester To a stirred suspension of 10.07 g (3R,4S,5S)-5-tert.-butoxycarbonyl-amino-3-(1-ethyl-propoxy)-4-trifluoromethanesulfonyloxy-cyclohex-1-enecarboxylic acid ethyl ester (20 mmol) and 50 ml 90% aqueous acetone were added 1.43 g sodium azide (22 mmol) and the reaction mixture was stirred at room temperature for 15 h. The acetone was removed by rotary evaporation (40° C./≧10 mbar) and the oily residue was distributed between 50 ml ethyl acetate and 25 ml 5% brine. The aqueous layer was extracted with 25 ml ethyl acetate and both organic layers were washed sequentially with 25 ml 5% brine. The combined organic layers were dried (Na$_2$SO$_4$) and the solvent was removed by rotary evaporation (40° C./≧10 mbar) affording 8.00 g light yellow, oily residue, which was dissolved in 80 ml hot hexane (50–60° C.), filtered and crystallized by cooling down and stirring at –20° C. over night. Filtration and washing with ca. 20 ml –20° C. cold hexane afforded after drying (50°/10 mbar/16 h) 6.15 g (77.6%) white, crystalline title product, m.p. 92–93° C.

[α]$_D$=–63.3° (CHCl$_3$; c=1)

EXAMPLE 12

Preparation of (3R,4R,5S)-4-acetylamino-5-tert.-butoxycarbonylamino-3-(1-ethyl-propoxy)-cyclohex-1-ene carboxylic acid ethyl ester A solution of 1.59 g (3R,4R,5S)-4-azido-5-tert.-butoxycarbonylamino-3-(1-ethyl-propoxy)-cyclohex-1-enecarboxylic acid ethyl ester (4 mmol) and 0.36 ml water (20 mmol) in 5 ml tetrahydrofuran was cooled to 0° C. 1.12 ml triethylamine (8 mmol) and 0.38 ml acetic anhydride were added and stirring at 0° C. was continued for 15 min. 1.14 ml tri-n-butyl phosphine (4.4 mmol) were added over 5 min. and the yellowish solution was stirred for 30 min. at 0° C. and then for 1 h at room temperature. After the addition of 5.58 ml triethylamine (40 mmol) 1.89 ml acetic anhydride (20 mmol) were added slowly under ice cooling and stirring at room temperature was continued for 1 h. The reaction mixture was diluted with 30 ml ethyl acetate and washed sequentially with 25 ml 2N HCl, 10 ml 10% $Na_2CO_3$ and 20 ml 10% brine. The aqueous layers were extracted sequentially with 20 ml ethyl acetate. The combined organic layers were dried ($Na_2SO_4$) and the solvent was removed by rotary evaporation (30° C./210 mbar) affording 2.89 g crude, which was purified by chromatography on $SiO_2$ (100 g) with hexane ethyl acetate 1.4:1 (100 ml fractions). Rotary evaporation (30° C./≧10 mbar) gave 1.39 g (84%) of the title product as a colorless, crystalline residue, m.p. 153.5–154.5° C. $[\alpha]_D$=−89.7° ($CHCl_3$; c=1)

EXAMPLE 13a
Preparation of (3R,4R,5S)-4-acetylamino-5-amino-3-(1-ethyl-propoxy)-cyclohex-1-enecarboxylic acid ethyl ester phosphoric acid salt To a solution of 10.31 g (3R,4R,5S)-4-acetylamino-5-tert.-butoxy-carbonyl-amino-3-(1-ethyl-propoxy)-cyclohex-1-enecarboxylic acid ethyl ester (25 mmol) in 100 ml ethyl acetate were added at room temperature. 25 ml 5N HCl in ethyl acetate. After 20 min. a white precipitate was formed and the thick suspension was stirred at room temperature for 24 h. The suspension was diluted with 125 ml ethyl acetate, washed with ca. 40 ml 3N NaOH (pH ca. 9.5) and 50 ml 10% brine. The aqueous layers were extracted sequentially twice with 125 ml, a total of 250 ml ethyl acetate. The combined organic layers were dried ($Na_2SO_4$) and the solvent was removed by rotary evaporation (30° C./≧10 mbar) affording 8.06 g (3R,4R,5S)-4-acetylamino-5-amino-3-(1-ethyl-propoxy)-cyclohex-1-enecarboxylic acid ethyl ester which was dissolved in 50 ml ethanol and added over ca. 2h to a warm solution (55° C.) of 2.45 g 99% phosphoric acid (25 mmol) in 50 ml ethanol. (After the addition of ca. ⅔ of (3R,4R,5S)-4-acetylamino-5-amino-3-(1-ethyl-propoxy)-cyclohex-1-enecarboxylic acid ethyl ester, the clear solution was seeded with pure title product). After cooling down and stirring at 0–5° C. for 3 h, the suspension was filtered, washed twice with 40 ml, a total of 80 ml acetone and dried (50° C./10 mbar/16 h) affording 9,07 g (88.4%) white, crystalline title product, m.p. 201–202° C.
$[\alpha]_D$=−32.1° ($H_2O$; c=1)

EXAMPLE 13b
Preparation of (3R,4R,5S)-4-acetylamino-5-amino-3-(1-ethyl-propoxy)-cyclohex-1-enecarboxylic acid ethyl ester phosphoric acid salt To a solution of 3.96 g (3R,4R,5S)-4-azido-5-tert.-butoxycarbonylamino-3-(1-ethylpropoxy)cyclohex-1-enecarboxylic acid ethylester (10 mmol) in 50 ml ethyl acetate were added 2.0 g wet Raney-Cobalt catalyst and the suspension was stirred and hydrogenated at room temperature for 20 h (~1.1 bar $H_2$; 500 rpm). After removing the catalyst by filtration, 1.53 ml triethylamine (11 mmol =1.11 g) and 0.99 ml acetic anhydride (10.5 mmol =1.07 g) were added all at once and the colorless solution was stirred at room temperature for 1 h. Then 5.26 ml 5.7 M HBr/acetic acid (30 mmol HBr) were added to the colorless solution and the reaction mixture was stirred at room temperature for 20 h. Then ca. 55 ml 2 N NaOH (pH ca. 9.5) were added under stirring and the organic layer was separated and washed twice with 30 ml, a total of 60 ml 20% brine. All three aqueous layers were extracted sequentially and twice with 30 ml, a total of 60 ml ethyl acetate and the combined organic layers were dried ($Na_2SO_4$). After filtration and removal of the solvent by rotary evaporation (50°/≧1 mbar) the yellowish, viscous residue (3.47 g) was dissolved in 20 ml ethanol and added under stirring to a 50° C. warm solution of 0.98 g ortho-phosphoric acid (10 mmol) in 40 ml ethanol over 30 min (after the addition of two third, the 50° C. warm solution was seeded with pure title product). The white suspension was cooled down (2 h) and stirred at 0° C. for 3 h. The crystals were filtered, washed with ca. 20 ml acetone and dried (50°/10 mbar/16 h) affording 3.41 g (83.2%) white, crystalline phosphoric acid salt, m.p. 198–199° C. (dec.).
$[\alpha]_D$=−32.1° ($H_2O$; c=1)

EXAMPLE 14
Preparation of all-cis-(1S,3R,4R,5R,6S)-5-(1-ethyl-propoxy)-4,6-dimethoxy-cyclohexane-1,3-dicarboxylic acid 1-ethyl ester)

To a suspension of 74.9 g all-cis-5-(1-ethyl-propoxy)-4,6-dimethoxy- cyclohexane-1,3-dicarboxylic acid diethyl ester (0.20 mol) in 240 ml cyclohexane was added 1.1 l 0.1 M glucose in water and 60 ml 0.1 M sodium phosphate buffer pH 7.0, and the mixture was heated to 35° C. under vigorous stirring. 560 mg Lipase from *Aspergillus oryzae* (Fluka 62285) was added and the emulsion/suspension kept at pH 7.0 and 35° C. by the controlled addition (pH-stat) of 1.0 N sodium hydroxide solution under vigorous stirring. After a total consumption of 187.5 ml 1.0 N sodium hydroxide (0.94 equivalents) after 20 h the pH was set to 2.0 with ca. 200 ml 1 N hydrochloric acid and the reaction mixture extracted with 1.5 l dichloromethane. The whole emulsion was filtered through a bed of 150 g Dicalite filter aid and the aqueous phase extracted again with 2×1.5 l dichloromethane which were passed through the Dicalite bed before use. Dicalite is a trade name for diatomaceous earth and perlite filtering materials as supplied by Grefco Minerals, USA The combined organic phases were dried on 175 g $Na_2SO_4$, filtered, concentrated (13 mbar/50° C./1 h) and the residue dried overnight on a high vacuum to give 69.42 g (100%) white crystalline title product, m.p. 147–148° C.
$[\alpha]D$=+7.4° ($CHCl_3$; c=1)

EXAMPLE 15
Preparation of all-cis-(1S,3R,4R,5R,6S)-5-(1-ethyl-propoxy)-4,6-dihydroxy-cyclohexane-1,3-dicarboxylic acid 1-ethyl ester)

To a stirred suspension of 30.0 g sodium iodide (0.20 mol) in 100 ml acetonitrile was added 21.7 g trimethyl-chlorsilane (0.20 mol; 25.3 ml) all at once. After stirring at room temperature for 0.5 h 17.3 g all-cis-5-(1-ethyl-propoxy)-4,6-dimethoxy-cyclohexane-1,3-dicarboxylic acid 1-ethyl ester (0.050 mol) were added and stirring at room temperature was continued for 12 h. The reaction mixture was distributed between 250 ml dichloromethane and 250 ml deionized water. After the two reddish phases were decolorized by the addition of ca. 0.25 g $Na_2S_2O_3$, the organic layer was washed twice with 100 ml, a total of 200 ml 10% brine. All aqueous layers were then extracted sequentially with 100 ml dichloromethane. The combined organic layers were dried over $Na_2SO_4$, filtered and the solvent was evaporated by rotary evaporation (50° C./≧1 mbar) affording 15.8 g (99.4%) of the title product as a colorless gum, which was used without purification in the next step.
$[\alpha]_D$=−7.2° ($CHCl_3$; c=1)

EXAMPLE 16
Preparation of all-cis-(1S,3R,4R,5R,6S)-7-(1-ethyl-propoxy)-6-hydroxy-2-oxo-octahydro-benzooxazole-5-carboxylic acid ethyl ester To a solution of 15.77 g all-cis-(1S,3R,4R,5R,6S)-5-(1-ethyl-propoxy)-4,6-dihydroxy-cyclohexane-1,3-dicarboxylic acid 1-ethyl ester (50 mmol) in 100 ml dichloromethane were added 5.06 g triethylamine (50 mmol) and 14.48 g diphenyl phosphoryl azide (50 mmol). The clear reaction mixture was then stirred under reflux for 16 h. After cooling down it was distributed between 100 ml dichloromethane and 150 ml 1M HCl. The organic layer was washed with 150 ml 5% NaHCO$_3$ and three times with 150 ml, a total of 450 ml 5% brine. All five aqueous layers were extracted sequentially twice with 100 ml, a total of 200 ml dichloromethane. The combined organic layers were dried with ca. 25 g Na$_2$SO$_4$, filtered and the solvent was evaporated by rotary evaporation (35° C./$\geq$10 mbar). The white, crystalline residue (17.4 g) was dissolved in 150 ml refluxing butyl acetate and crystallized by cooling down and stirring at −20° C. for 16 h. Filtration and washing with ca. 20 ml −20° C. cold butyl acetate afforded after drying (50° C./10 mbar/16 h) 12.6 g (79.9% over three steps) white, crystalline title product, m.p. 180.5–181° C.

$[\alpha]_D = -31.1°$ (CHCl$_3$; c=1)

What is claimed is:

1. A process for preparing a compound of formula

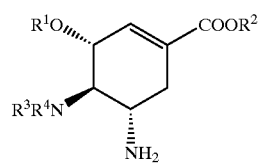

Ia wherein

R$^1$ is an optionally substituted alkyl group,

R$^2$ is an alkyl group and

R$^3$ and R$^4$, are independently selected from H and a substituent of an amino group, with the proviso that both R$^3$ and R$^4$ are not H simultaneously comprising:

hydrogenating an isophthalic acid derivative of formula II,

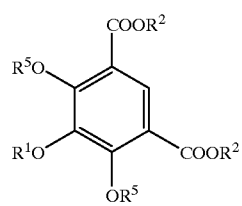

II wherein R$^1$ and R$^2$ are as above and R$^5$ is H thereby forming an all-cis-cyclohexane dicarboxylate of formula III,

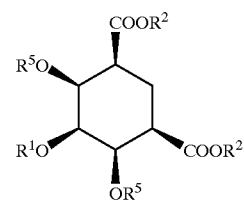

III wherein R$^1$, R$^2$ and R$^5$ are as above;

conducting an enzymatic stereo-selective hydrolysis and dealkylation sequence by hydrolyzing said all-cis-cyclohexane dicarboxylate of formula (III), forming said (S)-cyclohexane monoacid of formula IVa,

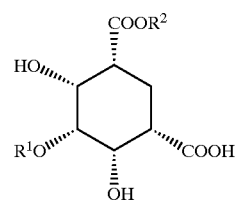

IVa wherein R$^1$ and R$^2$ are as above;

converting the cyclohexane monoacid of formula (IVa) to an oxazolidinone of the formula Va by a process selected from the group consisting of forming a cyclohexane monoamide from said cyclohexane monoacid, rearranging said cyclohexane monoamide to a cyclohexane isocyanate and cyclizing said cyclohexane isocyanate thereby forming said oxazolidinone Va and forming a cyclohexane acyl azide from said cyclohexane monoacid, rearranging said cyclohexane acyl azide to a cyclohexane isocyanate and cyclyzing said cyclohexane isocyante thereby forming said oxazolidinone Va;

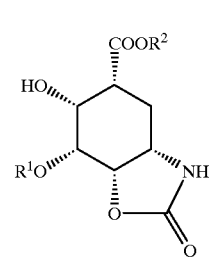

Va wherein R$^1$ and R$^2$ are as above;

transforming said oxazolidinone of formula (Va) into a cyclohexenol of formula VIa, by introducing an amino protecting group, and treating the protected amine with a suitable base thereby forming said cyclohexenol

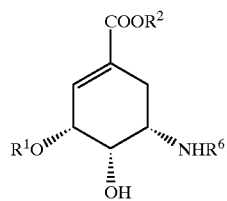

wherein $R^1$ and $R^2$ are as above and $R^6$ is an amino protecting group;

converting said cyclohexenol of formula (VIa) to an azide of formula VIIa, by sulfonylating the hydroxyl group to a sulfonic acid ester and displacing the sulfonic acid ester with a suitable azide nucleophile thereby forming

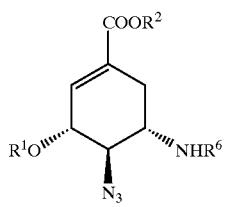

wherein $R^1$, $R^2$ and $R^6$ are as above;

reducing and acylating said azide of formula (VIIa) forming the respective acylated amine of the formula VIIIa,

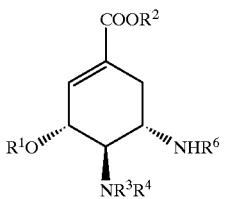

wherein $R^1$, $R^2$, $R^3$, $R^4$ and $R^6$ are as above; and removing the amino protecting group $R^6$ thereby forming said 4,5-diamino shikimic acid derivative of formula (Ia).

2. The process of claim 1 further comprising forming a pharmaceutically acceptable salt of the 4,5-diamino shikimic acid derivative of formula Ia.

3. The process of claim 1, wherein said hydrogenating step for forming said all-cis-cyclohexane dicarboxylate of formula III is performed in the presence of a hydrogenation catalyst at a temperature between about 20° C. and about 150° C. and at a hydrogen pressure between about 1 bar and about 200 bar.

4. Process of claim 3, wherein said hydrogenation catalyst is selected from the group consisting of rhodium and ruthenium applied in an amount of between about 1 to about 10% on an inert support.

5. Process of claim 1, wherein said stereo-selective hydrolysis step for obtaining the (S)-cyclohexane monoacid of formula (IVa) from the all-cis cyclohexane dicarboxylate of formula III with $R^5$=H further comprises selecting and using an esterase of the EC class 3.1.1.1.

6. Process of claim 5, further comprising selecting a pig liver esterase.

7. Process of claim 1 wherein said transforming of cyclohexane monoacid of formula IVa into the oxazolidinone uses a reaction selected from the group consisting of a Curtius degradation, a Yamada Curtius degradation and a Hoffmann degradation.

8. Process of claim 1, wherein a base for said base induced transformation of said amino protected oxazolidinone into said cyclohexenol (VIa) is selected from the group consisting of an alkali-hydride, an alkali-alcoholate, a diazabicycloundecen and a tetra-alkylguanidine.

9. Process of claim 1, wherein said azide nucleophile for displacing said sulfonic acid ester is an alkali azide.

10. Process of claim 1 wherein said reduction of said azide (VIIa) comprises selecting and using a reduction method selected from the group consisting of a metal catalyzed hydrogenation and a phosphine in the presence of water.

11. Process of claim 1, wherein said acylation comprises an acetylation.

* * * * *